United States Patent [19]

Kikuchi et al.

[11] Patent Number: 5,654,483
[45] Date of Patent: Aug. 5, 1997

[54] PROCESS FOR PRODUCING ALKOXY-SUBSTITUTED TRIPHENYLAMINES

[75] Inventors: Chiyuki Kikuchi; Hiroshi Naruse; Masaru Wada; Teruyuki Nagata, all of Fukuoka-ken, Japan

[73] Assignee: Mitsui Toatsu Chemicals, Inc., Tokyo, Japan

[21] Appl. No.: 575,091

[22] Filed: Dec. 19, 1995

[30] Foreign Application Priority Data

Dec. 26, 1994 [JP] Japan ................... 6-322795
Dec. 26, 1994 [JP] Japan ................... 6-322797

[51] Int. Cl.$^6$ .................. C07C 209/04; C07C 209/18
[52] U.S. Cl. ............ 564/435; 564/433; 564/397; 564/398
[58] Field of Search ..................... 564/433, 435, 564/397, 398

[56] References Cited

U.S. PATENT DOCUMENTS

| | | | |
|---|---|---|---|
| 5,344,987 | 9/1994 | Immel et al. | 564/435 |
| 5,449,829 | 9/1995 | Kusuda et al. | 564/397 |
| 5,545,752 | 8/1996 | Nagata et al. | 564/398 |

OTHER PUBLICATIONS

Nagata et al., Chemical Abstracts, vol. 105, abstract 226014f 1986.

*Primary Examiner*—Richard L. Raymond
*Attorney, Agent, or Firm*—Burns, Doane, Swecker & Mathis

[57] ABSTRACT

A process for producing an alkoxy-substituted triphenylamine comprising reacting an alkoxy-substituted cyclohexanone with a diphenylamine or an aniline, while forming said cyclohexanone in the same system from an alkoxy-substituted phenol by using said phenol as a hydrogen acceptor, in the presence of a hydrogen transfer catalyst and a catalytic amount of the alkoxy-substituted cyclohexanone corresponding to the alkoxy-substituted phenol used for the reaction, or after converting partially the alkoxy-substituted phenol to a catalytic amount of the alkoxy-substituted cyclohexanone under a hydrogen pressure in the presence of a hydrogen transfer catalyst, wherein a surface-supported catalyst is used as the hydrogen transfer catalyst.

14 Claims, No Drawings

PROCESS FOR PRODUCING ALKOXY-SUBSTITUTED TRIPHENYLAMINES

BACKGROUND OF THE INVENTION

1. Field of the Invention

The present invention relates to an improved process for producing alkoxy-substituted triphenylamines.

The alkoxy-substituted triphenylamines obtained by the process of the present invention are useful compounds as an intermediate for use in general chemical industries, particularly as an intermediate for dyes, agricultural chemicals, rubber chemicals and the like.

2. Description of the Related Art

It has hitherto been known to prepare triphenylamines by reacting cyclohexanones with diphenylamines, while forming the cyclohexanones in the same system from phenols used as the hydrogen acceptor in the presence of a hydrogen transfer catalyst (Japanese Patent Laid-Open No. 183250/1986). The reference describes that triphenylamine is obtained in an yield of 68.5% (selectivity: 85.1%) by reacting diphenylamine with cyclohexanone in an excess amount of phenol in the presence of a palladium catalyst.

However, when the present inventors traced the above-described process by using an alkoxy-substituted cyclohexanone and an alkoxy-substituted phenol as raw materials, they found that a triphenylamine with the alkoxy substituent eliminated was by-produced in a considerable amount, but an alkoxy-substituted triphenylamine, the desired product, could not be obtained in a satisfactorily high yield.

SUMMARY OF THE INVENTION

It is an object of the present invention to provide a highly efficient process for producing an alkoxy-substituted triphenylamine in a high yield from an alkoxy-substituted phenol and a diphenylamine or an aniline.

The present inventors have made an examination to establish a more industrially advantageous process for producing alkoxy-substituted triphenylamines. In the course of the examination, it was found that in the process of reacting an alkoxy-substituted cyclohexanone with a diphenylamine or an aniline, while forming the cyclohexanone in the same system from an alkoxy-substituted phenol by using the phenol as a hydrogen acceptor, in the presence of a hydrogen transfer catalyst and a catalytic amount of the alkoxy-substituted cyclohexanone corresponding to the alkoxy-substituted phenol used for the reaction, or in the process of converting an alkoxy-substituted phenol to a catalytic amount of the corresponding alkoxy-substituted cyclohexanone under a hydrogen pressure and continuously reacting the alkoxy-substituted cyclohexanone with a diphenylamine or an aniline, while forming the cyclohexanone in the same system from the remaining alkoxy-substituted phenol by using the phenol as a hydrogen acceptor, in the absence of the catalytic amount of the alkoxy-substituted cyclohexanone in the beginning but in the presence of a hydrogen transfer catalyst, a decomposition reaction, i.e., a dealkoxylation proceeded so that the yield of an alkoxy-substituted triphenylamine, the desired product, was reduced. Further, it was surprisingly found that a surface-supported catalyst controlled the dealkoxylation and was significantly effective also as the hydrogen transfer catalyst, and when the surface-supported catalyst was used as the hydrogen transfer catalyst in the above reaction, alkoxy-substituted triphenylamines, the desired products, could be obtained in high yields. The present invention has been completed on the basis of these findings.

Specifically, the present invention provides a process for producing an alkoxy-substituted triphenylamine comprising reacting an alkoxy-substituted cyclohexanone with a diphenylamine or an aniline, while forming the cyclohexanone in the same system from an alkoxy-substituted phenol by using the phenol as a hydrogen acceptor, in the presence of a hydrogen transfer catalyst and a catalytic amount of the alkoxy-substituted cyclohexanone corresponding to the alkoxy-substituted phenol used for the reaction, wherein a surface-supported catalyst is used as the hydrogen transfer catalyst.

The present invention also provides a process for producing an alkoxy-substituted triphenylamine comprising converting partially an alkoxy-substituted phenol to the corresponding alkoxy-substituted cyclohexanone under hydrogen pressure and continuously reacting the alkoxy-substituted cyclohexanone with a diphenylamine or an aniline while forming the cyclohexanone in the same system from the remaining alkoxy-substituted phenol by using the phenol as a hydrogen acceptor, in the presence of a hydrogen transfer catalyst, wherein a surface-supported catalyst is used as the hydrogen transfer catalyst.

According to the process of the present invention, the dealkoxylation of raw materials and the intermediates can be controlled by using a surface-supported catalyst as the hydrogen transfer catalyst, and therefore desired alkoxy-substituted triphenylamines can be obtained in high yields.

DETAILED DESCRIPTION OF THE PREFERRED EMBODIMENTS

The present invention will be described in detail hereinbelow.

The alkoxy-substituted phenol used in the process of the present invention is a phenol having at least one alkoxy group and may have other substituent or substituents, such as alkyl group, phenyl group, phenoxy group, cyclohexyl group and fluorine atom, in addition to the alkoxy group or groups.

The alkoxy-substituted phenol may include, for example, 4-methoxyphenol, 2-methoxyphenol, 4-ethoxyphenol, 4-butoxyphenol, 4-nonyloxyphenol, 2,4-dimethoxyphenol, 3-methyl-4-methoxyphenol, 2-methoxy-4-phenylphenol, 3-methyl-4-butoxyphenol, 2-methoxy-4-phenoxyphenol, 2-methoxy-4-cyclohexylphenol and 2-fluoro-4-methoxyphenol. However, the alkoxy-substituted phenol is not limited to only those illustrated above.

Regarding the amount of the alkoxy-substituted phenol used in the process of the present invention, no problem will arise as long as it is equivalent or more to that of a diphenylamine where the corresponding alkoxy-substituted cyclohexanone is present from the beginning and the diphenylamine is used as a raw material. However, when the alkoxy-substituted phenol is used in excess also as a solvent, the selectivity to the triphenylamine tends to be increased. Therefore, it is preferable to use the alkoxy-substituted phenol in an amount of 1.5 to 20 times, preferably 2 to 10 times by mole of the diphenylamine. Where an aniline is used, no particular problem will be raised as long as the alkoxy-substituted phenol is used in two equivalents or more to the aniline. Also in this case, however, the selectivity tends to be increased by using the phenol in excess also as a solvent. Therefore, it is preferable to use the phenol in an amount of 3 to 20 times, preferably 4 to 10 times by mole of the aniline.

The alkoxy-substituted phenol used in the process of the present invention is a hydrogen acceptor and is also the source of supply for the alkoxy-substituted cyclohexanone formed as a result of the acceptance of hydrogen. Accordingly, the hydrogen by-produced during the reaction is used within the system. Further, the alkoxy-substituted phenol containing the alkoxy-substituted cyclohexanone which has been separated on removing the desired product of an alkoxy-substituted triphenylamine can be reused by recycling it to the reaction system as the mixture. Even when a suitable alkoxy-substituted cyclohexanone corresponding to the desired alkoxy-substituted triphenylamine is hardly obtainable, if the corresponding alkoxy-substituted phenol is available, the reaction may be effected by using an excess amount of the alkoxy-substituted phenol, reacting hydrogen fed in advance with a part of the phenol to convert it into the corresponding cyclohexanone, and reacting concurrently or subsequently the cyclohexanone with a diphenylamine or an aniline. Thus, the process of the present invention has a number of merits including a wide scope of applications.

As the alkoxy-substituted cyclohexanone, there are used alkoxy-substituted cyclohexanones corresponding to the above-described alkoxy-substituted phenols. They may include, for example, 4-methoxycyclohexanone, 2-methoxycyclohexanone, 4-ethoxycyclohexanone, 4-butoxycyclohexanone, 4-nonyloxycyclohexanone, 2,4-dimethoxycyclohexanone, 3-methyl 4-methoxycyclohexanone, 2-methoxy-4-phenylcyclohexanone, 3-methyl-4-butoxycyclohexanone, 2-methoxy-4-phenoxycyclohexanone, 2-methoxy-4-cyclohexylcyclohexanone, and 2-fluoro-4-methoxycyclohexanone. However, the alkoxy-substituted cyclohexanone is not limited to only those described above, as is the case with the alkoxy-substituted phenol.

The amount of the alkoxy-substituted cyclohexanone to be used is a catalytic amount of 0.03 mole or more for each mole of a diphenylamine where the diphenylamine is used as a raw material. Where an aniline is used, there is no particular problem as long as the amount is a catalytic amount of 0.03 mole or more for each mole of the aniline. It is however preferable to use the cyclohexanone in an amount of 0.05 to 0.60 mole for each mole of the diphenylamine and 0.05 to 1.00 mole for each mole of the aniline.

The diphenylamine used as a raw material in the process of the present invention may be any diphenylamine known in the art. It may be unsubstituted or substituted by an alkyl group, alkoxy group, phenyl group, phenoxy group, cyclohexyl group, carboxyl group, hydroxyl group, fluorine atom and the like. For example, it may include diphenylamine, diphenylamines whose nuclei are substituted by one or more alkyl groups, such as 2-methyldiphenylamine, 3-methyldiphenylamine and 2,2'-dimethyldiphenylamine, similarly diphenylamines whose nuclei are substituted by one or more alkoxy groups, halogens, carboxyl groups or nitrile groups, and p-phenyldiphenylamine. Diphenylamines whose nuclei are substituted by different functional groups, such as 2-methyl-4-chlorodiphenylamine, may also be used.

The aniline used as a raw material in the process of the present invention may be any aniline known in the art. It may be unsubstituted or substituted by an alkyl group, alkoxy group, phenyl group, phenoxy group, cyclohexyl group, carboxyl group, hydroxyl group, fluorine atom or the like. For example, it may include aniline, alkyl-substituted anilines such as 2-methylaniline, 3-methylaniline and 4-methylaniline, alkoxy-substituted anilines such as 4-methoxyaniline, carboxy-substituted anilines such as 4-carboxyaniline, and p-phenylaniline. Anilines whose nucleus is substituted by different functional groups, such as 2-methyl-4-chloroaniline, may also be used.

In the process of the present invention, it is important to use a surface-supported catalyst (egg shell type) as the hydrogen transfer catalyst. Specifically, it includes surface-supported catalysts carrying nickel, surface-supported catalysts carrying cobalt, surface-supported catalysts carrying copper, surface-supported catalysts which carry a metal of Group 8 in the Periodic Table, surface-supported catalysts carrying rhenium and the like. Among those, surface-supported palladium catalysts are preferred. Particularly, catalysts having palladium supported on the surface of a carrier, such as surface-supported palladium-carbon, surface-supported palladium-silica, surface-supported palladium-alumina, surface-supported palladium-diatomaceous earth and surface-supported palladium-magnesia are preferred. Especially, surface-supported palladium-carbon catalysts are most preferred.

Then, the surface-supported catalyst is illustrated by reference to palladium-carbon (Pd/C). The conventional uniform-type Pd/C is prepared by impregnating completely carbon as a carrier with an aqueous solution of a water-soluble palladium compound. On the contrary, the surface-supported catalyst is obtained by drying a carrier completely, spraying on the carrier an aqueous solution of a water-soluble palladium compound such as palladium chloride and palladium acetate or adding dropwise an aqueous solution of the palladium compound while stirring the carrier moderately to impregnate only the surface layer of the carrier with the palladium compound, drying the resultant carrier, reducing the palladium compound with hydrazine, formalin or formic acid in a liquid phase or with hydrogen in a gas phase, washing the carrier with hot water, and drying the carrier. Thus, there can be obtained a palladium-carbon catalyst which carries palladium only in the surface layer thereof.

The use of the catalyst is effective in controlling the formation of by-products due to the elimination of alkoxy groups, leading to the accomplishment of a high selectivity to the desired product.

The reaction of the present invention is illustrated by the following reaction formulas where a methoxy-substituted phenol and aniline are used by way of example.

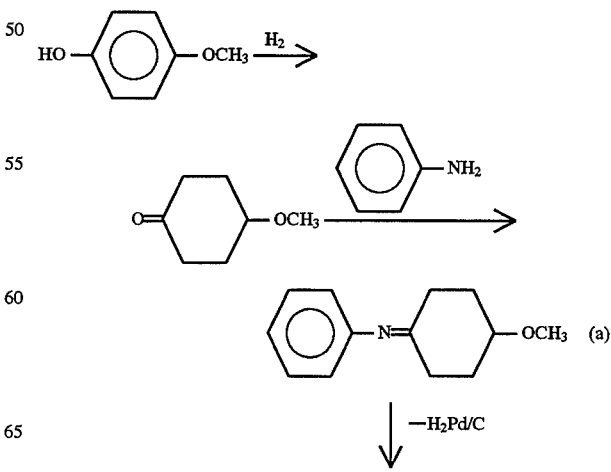

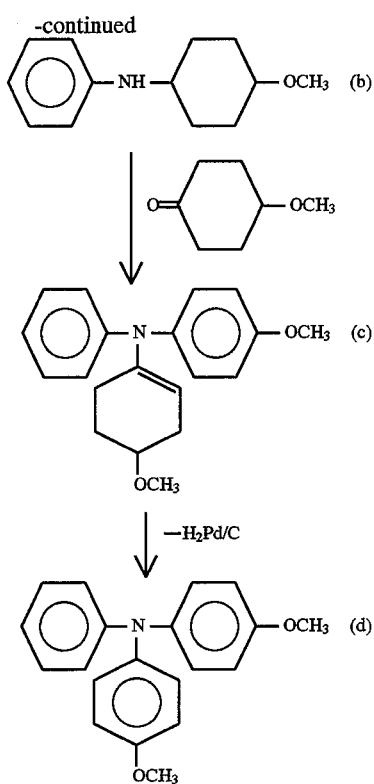

According to the examination by the present inventors, it has become apparent that the dealkoxylation reaction primarily proceeds not in the phase of compounds (b) and (d) and the starting material of 4-methoxyphenol, in which one or more alkoxy groups are bonded to one or more aromatic rings, but in the phase of compounds (a) and (c) and 4-methoxycyclohexanone, in which each alkoxy group is bonded to an aliphatic carbon. Since the dehydrogenation reaction in compounds (a) and (c) proceeds favorably by any catalyst of either the uniform-type or the surface-supported type, it is thought that the dehydrogenation reaction takes place in the surface section of the catalyst, while the dealkoxylation reaction occurs in the deep layer section thereof. After all, because of a high degree of freedom of the alkoxy groups bonded to the aliphatic carbons, it is possible that the alkoxy groups arrive at the bottom of pores of the catalyst, in other words, the deep layer section of the catalyst, as compounds (a) and (c) approach the catalyst. Therefore, it is thought that in the case of the uniform-type catalyst which carries palladium to the depth of the deep layer section of the carrier, the alkoxy groups having arrived at the deep layer section are subjected to dealkoxylation by the palladium carried, whereas in the case of the surface-supported catalyst which carries no palladium in the deep layer section of the carrier, the dealkoxylation reaction is controlled so that an alkoxy-substituted triphenylamine, the desired product, can be obtained with a high selectivity.

The amount of the catalyst used is generally 0.001 to 0.2 atomic gram, preferably 0.004 to 0.1 atomic gram in terms of its metallic atom based on a diphenylamine to be used as a raw material, or it is generally 0.001 to 0.2 atomic gram, preferably 0.004 to 0.1 atomic gram in terms of the metallic atom based on an aniline to be used as a raw material.

The surface-supported catalyst used in the present invention is a solid metal catalyst in which a metal is preferably supported on a carrier powder at a amount of about 0.5 to 10% by weight based on the carrier powder. The solid metal catalyst is an egg-shell type catalyst having at least 70% by weight of the metal supported within 2 μm from the surface of the carrier. More preferably, the catalyst has at least 80% by weight of the metal supported within 1 μm from the surface of the carrier. The metal supported state can be analyzed by use of EPMA (Electron Probe Micro-analyzer).

In the process of the present invention, it is preferable to recycle and reuse repeatedly and continuously the reaction liquid obtained by separating the desired product from the reaction mass having undergone the reaction, without separating the remaining alkoxy-substituted cyclohexanone from the reaction liquid. In this case, it is advantageous to use an excess amount of the alkoxy-substituted phenol also as a solvent. Although it is not necessary to use other reaction solvents, they may be used without any trouble, as a matter of course. The reaction temperature selected is generally in the range of 130° to 300° C., preferably in the range of 180° to 250° C. If the temperature is below the range, the reaction rate is small and a large number of by-products tend to be formed.

In the process of the present invention, a preferred embodiment of charging the raw materials into a reaction vessel is such that a catalyst and an alkoxy-substituted phenol are charged, stirred and heated in the vessel in advance, to which a diphenylamine or an aniline is added dropwise to cause the reaction.

It is advantageous to carry out the reaction while removing the water formed. Therefore, the water is suitably separated from the reaction mixture by an azeotropic distillation using a solvent such as benzene, toluene or xylene.

The produced alkoxy-substituted triphenylamine can be obtained by treating the mixture having undergone the reaction by a conventional procedure such as distillation, crystallization and extraction. For example, the reaction liquid having undergone the reaction is filtered to separate the catalyst. The catalyst thus recovered can be used again. Then, the filtrate is concentrated to recover, as a distillate, the excess amount of the alkoxy-substituted phenol and the alkoxy-substituted cyclohexanone involved therein, and the distillate is recycled to the reaction system as the mixture. The concentrated residue in the concentrator is further subjected to distillation, crystallization or the like to purify and separate the triphenylamine.

Now, the present invention will be described in detail with reference to the following examples, but the scope of the present invention should not be limited only to these examples.

EXAMPLE 1

In a round flask provided with a reflux condenser equipped with a separator, a thermometer and a stirrer were charged 1.23 g of a surface-supported 5% Pd/C (at least 80% by weight of the carried Pd was supported within 1 μm from the surface of active carbon: 50 wet %) manufactured by N. E. Chemcat Co., 62.07 g (0.5 mol) of p-methoxyphenol, 3.85 g (0.03 mol) of p-methoxycyclohexanone and 22.93 g (0.1 mol) of 4,4'-dimethoxydiphenylamine. While being stirred, the contents in the reactor were heated to 200° C. and reacted for 9 hours and further heated to 230° C. and reacted for 4 hours. The water thus formed was azeotropically distilled by the addition of toluene, condensed in the reflux condenser and then separated by the separator. Subsequently, the reaction liquid was cooled and the 5% Pd/C was separated by filtration from the liquid, reaction mixture. The filtrate was analyzed by means of gas chromatography. As a result, the conversion of the 4,4'-dimethoxydiphenylamine was found to be 99.2%, and the selectivity of 4,4',4"-trimethoxytriphenylamine was 91.5%. Further, the selectivity of its dealkoxylated compound, 4,4'-dimethoxytriphenylamine, was 5.4%.

EXAMPLES 2 to 6

The reaction was carried out in the same manner as in Example 1 using a variety of diphenylamines and phenols given in Table 1 and cyclohexanones corresponding to the phenols. The results are illustrated in Table 1.

TABLE 1

| Example | Diphenylamine | Phenol | Conversion (mol %) | Selectivity (mol %) |
|---|---|---|---|---|
| 2 | 2-methyl-diphenylamine | 4-methoxyphenol | 93.2 | 82.4 |
| 3 | diphenylamine | 4-methoxyphenol | 97.5 | 86.2 |
| 4 | diphenylamine | 2-methoxyphenol | 88.6 | 83.5 |
| 5 | ditolylamine | 4-methoxyphenol | 96.5 | 84.9 |
| 6 | 4-methoxy-diphenylamine | 4-methoxyphenol | 97.0 | 83.7 |

EXAMPLE 7

In an stainless steel autoclave with an internal volume of 500 ml were charged 91.7 g (0.4 mol) of 4,4'-dimethoxydiphenylamine, 248.3 g (2.0 mol) of 4-methoxyphenol and 4.92 g of a surface-supported 5% Pd/C (at least 80% by weight of the carried Pd was supported within 1 μm from the surface of active carbon: 50 wet %) manufactured by N. E. Chemcat Co. After replacing the air in the autoclave with nitrogen, the autoclave was pressurized to 10 kg/cm²G with hydrogen. Continuously, the contents were reacted by heating and treated in the same manner as in Example 1. As a result, the selectivity of 4,4',4"-trimethoxytriphenylamine was 81.7%. Simultaneously, the selectivity of 4,4'-dimethoxytriphenylamine, the dealkoxylated compound, was 10.7%.

Comparative Example 1

The reaction and the treatment were carried out in the same manner as in Example 1 except that a uniform type 5% Pd/C which was not of the surface-supported type and was manufactured by N. E. Chemcat Co. was used as the hydrogen transfer catalyst. As a result, the conversion of the 4,4'-dimethoxydiphenylamine was 75.2%, while the selectivity of 4,4',4"-trimethoxytriphenylamine was 71.8%. Simultaneously, the selectivity of 4,4'-dimethoxytriphenylamine, the dealkoxylated compound, was 19.4%.

EXAMPLE 8

In a 200-ml round flask provided with a reflux condenser equipped with a separator, a thermometer and a stirrer were charged 1.23 g of a surface-supported 5% Pd/C (at least 80% by weight of the carried Pd was supported within 1 μm from the surface of active carbon: 50 wet %) manufactured by N. E. Chemcat Co., 99.31 g (0.8 mol) of p-methoxyphenol and 6.41 g (0.05 mol) of 4-methoxycyclohexanone, and separately 12.32 g (0.1 mol) of 4-methoxyaniline were charged in a dropping apparatus. While being stirred, the contents in the reactor were heated to 200° C., to which the 4-methoxyaniline in the dropping apparatus was added dropwise over 7 hours while maintaining the contents at the same temperature under stirring. After completion of the dropping, the contents were further heated to 220° C. at which they were reacted for 9 hours. The water thus formed was azeotropically distilled by the addition of toluene, condensed in the reflux condenser and separated by the separator. Then, the reaction liquid was cooled, and the 5% Pd/C was separated by filtration from the liquid reaction mixture. The filtrate was analyzed by means of gas chromatography. As a result, the conversion of the 4-methoxyaniline was found to be 99.0%, and the selectivity of 4,4',4"-trimethoxytriphenylamine was 84.4%. Simultaneously, the selectivity of 4,4'-dimethoxytriphenylamine, the dealkoxylated compound, was 12.2%.

EXAMPLES 9 to 13

The reaction was carried out in the same manner as in Example 8, using a variety of anilines and alkoxy-substituted phenols given in Table 2 and alkoxy-substituted cyclohexanones corresponding to the alkoxy-substituted phenols. The results are illustrated in Table 2.

TABLE 2

| Example | Aniline | Phenol | Conversion (mol %) | Selectivity (mol %) |
|---|---|---|---|---|
| 9 | 2-methylaniline | 4-methoxyphenol | 95.2 | 83.4 |
| 10 | aniline | 4-methoxyphenol | 99.5 | 86.9 |
| 11 | aniline | 2-methoxyphenol | 90.2 | 82.7 |
| 12 | 4-methylaniline | 4-methoxyphenol | 99.5 | 87.9 |
| 13 | 4-methoxy-aniline | 4-methoxyphenol | 98.5 | 83.2 |

EXAMPLE 14

In a stainless steel autoclave with an internal volume of 500 ml were charged 223.5 g (1.8 mol) of 4-methoxyphenol and 4.92 g of a surface-supported 5% Pd/C (at least 80% by weight of the carried Pd was supported within 1 μm from the surface of active carbon: 50 wet %) manufactured by N. E. Chemcat Co., and separately 24.6 g (0.2 mol) of 4-methoxyaniline were charged in a dropping apparatus. After replacing the air in the autoclave with nitrogen, the autoclave was pressurized to 10 kg/cm²G with hydrogen. Continuously, the contents were reacted by heating and treated in the same manner as in Example 8. As a result, the conversion of the 4-methoxyaniline was 88.5%, and the selectivity of 4,4',4"-trimethoxytriphenylamine was 80.9%. Simultaneously, the selectivity of 4,4'-dimethoxytriphenylamine, the dealkoxylated compound, was 13.5%.

Comparative Example 2

The reaction and the treatment were carried out in the same manner as in Example 8 except that a uniform type 5% Pd/C which was not of the surface-supported type and was manufactured by N. E. Chemcat Co. was used as the hydrogen transfer catalyst. As a result, the conversion of the 4-methoxyaniline was 98.3% and the selectivity of 4,4',4"-trimethoxytriphenylamine was 54.8%. Simultaneously, the selectivity of 4,4'-dimethoxytriphenylamine, the dealkoxylated compound, was 23.5%.

What is claimed is:

1. A process for producing an alkoxy-substituted triphenylamine comprising reacting an alkoxy-substituted cyclohexanone with a diphenylamine, while forming said cyclohexanone in the same system from an alkoxy-substituted phenol by using said phenol as a hydrogen acceptor, in the presence of a hydrogen transfer catalyst and a catalytic amount of the alkoxy-substituted cyclohexanone corresponding to the alkoxy-substituted phenol used for the reaction, wherein a surface-supported catalyst is used as the hydrogen transfer catalyst.

2. The process according to claim 1, wherein the surface-supported catalyst is a catalyst composed of palladium supported on a carrier.

3. The process according to claim 2, wherein the carrier is carbon.

4. The process according to claim 1, wherein the diphenylamine is an alkoxy-substituted diphenylamine.

5. A process for producing an alkoxy-substituted triphenylamine comprising reacting an alkoxy-substituted cyclohexanone with an aniline, while forming said cyclohexanone in the same systems form an alkoxy-substituted phenol by using said phenol as a hydrogen acceptor, in the presence of a hydrogen transfer catalyst and a catalytic amount of the alkoxy-substituted cyclohexanone corresponding to the alkoxy-substituted phenol used for the reaction, wherein a surface-supported catalyst is used as the hydrogen transfer catalyst.

6. The process according to claim 5, wherein the reaction is effected while adding the aniline dropwise.

7. The process according to claim 5, wherein the aniline is an alkoxy-substituted aniline.

8. A process for producing an alkoxy-substituted triphenylamine comprising converting partially an alkoxy-substituted phenol to a catalytic amount of the corresponding alkoxy-substituted cyclohexanone under a hydrogen pressure and continuously reacting, the alkoxy-substituted cyclohexanone with a diphenylamine while forming said cyclohexanone in the same system from the remaining alkoxy-substituted phenol by using said phenol as a hydrogen acceptor, in the presence of a hydrogen transfer catalyst, wherein a surface-supported catalyst is used as the hydrogen transfer catalyst.

9. The process according to claim 8, wherein the surface-supported catalyst is a catalyst composed of palladium supported on a carrier.

10. The process according to claim 9, wherein the carrier is carbon.

11. The process according to claim 8, wherein the diphenylamine is an alkoxy-substituted diphenylamine.

12. A process for producing an alkoxy-substituted triphenylamine comprising converting partially an alkoxy-substituted phenol to a catalytic amount of the corresponding alkoxy-substituted cyclohexanone under a hydrogen pressure and continuously reacting the alkoxy-substituted cyclohexanone with an aniline while forming said cyclohexanone in the same system from the remaining alkoxy-substituted phenol by using said phenol as a hydrogen acceptor, in the presence of a hydrogen transfer catalyst, wherein a surface-supported catalyst is used as the hydrogen transfer catalyst.

13. The process according to claim 12, wherein the reaction is effected by adding the aniline dropwise.

14. The process according to claim 12, wherein the aniline is an alkoxy-substituted aniline.

* * * * *